United States Patent [19]

Wu

[11] Patent Number: 5,047,395

[45] Date of Patent: Sep. 10, 1991

[54] REDUCTION OF OXYRADICAL DAMAGE IN BIOMEDICAL APPLICATIONS

[75] Inventor: Tai-Wing Wu, Toronto, Canada

[73] Assignee: Nagase Co., Ltd., Osaka, Japan

[21] Appl. No.: 554,197

[22] Filed: Jul. 17, 1990

[51] Int. Cl.$^5$ .................. A61K 37/00; A61K 31/40
[52] U.S. Cl. ............................... 514/2; 514/12; 514/21; 514/422; 514/424; 514/427
[58] Field of Search .................. 514/2, 12, 21, 427

[56] References Cited

U.S. PATENT DOCUMENTS 4,877,810 10/1989 Mickle et al. .................. 514/456

OTHER PUBLICATIONS

Stoker et al., 1989 *Biochim. Biophys. Acta* 213:353-357.

*Primary Examiner*—Frederick E. Waddell
*Assistant Examiner*—Terry Wilson
*Attorney, Agent, or Firm*—Wyatt, Gerber, Burke and Badie

[57] ABSTRACT

The biliproteins delta-bilirubin and delta-bilipeptide are useful as a cytoprotective antioxidants. Delta-bilipeptide as the term is used herein is a truncated form of delta-bilirubin in which an albumin analogue of 10–200 amino acid residues replaces the albumin portion of delta-bilirubin. Patient-administrable compositions for addition to a patient's blood to minimize oxyradical damage caused by ischemia-reperfusion injury that may result in various surgical procedures, and comprising delta-bilirubin or delta-bilipeptide, are described.

20 Claims, 1 Drawing Sheet

REDUCTION OF OXYRADICAL DAMAGE IN BIOMEDICAL APPLICATIONS

FIELD OF THE INVENTION

The present invention generally relates to antioxidants which are biomedically applicable. More particularly, the present invention relates to the oxy-radical scavenging properties of protein- or peptide-bound bilirubins.

BACKGROUND OF THE INVENTION

Bilirubins are breakdown products of heme. There are four main types of bilirubin, namely, unconjugated bilirubin ($B_u$), mono- or di-sugar-conjugated bilirubin and delta-bilirubin.

Delta-bilirubin comprises bilirubin covalently linked to albumin via a peptide bond between a propionic acid side chain of the tetrapyrrole group of bilirubin, and an epsilon amino group of a lysine residue in albumin. This lysine residue is located between amino acid residues 97 and 224, in the N-terminal half of the protein, i.e. from the N-terminus of the albumin protein. Delta-bilirubin is thus often referred to as a biliprotein, BP. Delta-bilirubin is the most polar form and the most water soluble form of bilirubin. It is also the most stable form of bilirubin and thus, delta-bilirubin is not as sensitive as other forms of bilirubin to the effects of heat, light, air, and acid or alkaline hydrolysis.

Oxygen free radicals, such as the superoxide radical $O_2$. and hydroxyl radical OH. are formed by approximately 5% of the oxygen in the bloodstream. Such oxyradicals are highly toxic and can cause irreversible oxidative damage to cells and tissue. When regular blood flow to a living organ or tissue is interrupted, e.g. during organ transplantation, by-pass surgery and the like (the surgical procedure known as ischemia), the reintroduction of oxygen into the tissue leads to a vast increase in superoxide production, leading to the formation of secondary hydroxyl radicals and marked cellular toxicity. The primary source of the excess free radicals produced after ischemia is xanthine dehydrogenase, an enzyme that normally transfers electrons from purine bases to the oxidized form of nicotinamide adenine dinucleotide. During hypoxia this enzyme is rapidly and irreversibly converted to xanthine oxidase, an enzyme that generates large quantities of superoxide by transferring its electrons directly to oxygen.

Oxygen free radicals can attack and damage important biological molecules. Within cellular membranes, OH. can initiate a chain reaction known as lipid peroxidation, in which polyunsaturated fatty acids are broken down into water soluble products with consequent disruption of membrane integrity. Peroxidation of lysosomal membranes may result in cell death through the release of lysosomal hydrolases into the cytoplasm. Oxygen radicals can produce mutations in DNA and depolymerise hyaluronic acid and related macro molecules.

The body has several defense mechanisms by which oxidative damage can be minimized. One is an enzymatic mechanism which involves superoxide dismutase, which catalyses the combination of two $O_2$. free radicals with hydrogen to form hydrogen peroxide, a less toxic molecule which is eliminated by a peroxidase such as catalase. Another defense mechanism is provided by natural antioxidants such as vitamin E (tocopherol) within the hydrophobic core of cell membranes, and glutathione and ascorbic acid in the cell water. Such antioxidants are adequate to detoxify most of the superoxide normally produced within the cell. However they cannot cope with the vastly increased superoxide production which occurs when oxygen is reintroduced into a tissue after a period of ischemia.

There is therefore a need for a therapeutically effective antioxidant in order to prevent or minimize oxyradical damage that may follow surgical procedures, specifically surgery involving ischemia of organs such as the heart, liver and kidney.

BRIEF DISCUSSION OF THE PRIOR ART

Stocker et al. (Science 235: 1943-1946; 1987) suggest that free or unconjugated bilirubin Bu may be a physiologically significant antioxidant. Bilirubin significantly inhibited the rate of radical-induced oxidation of linoleic acid in homogeneous solutions. However, not only was this research conducted in a non-physiological cell-free system, for example, organic solvents and liposomes, but also the range of $B_u$ utilized included quantities of $B_u$ known to be cytotoxic.

Stocker et al. (Proc. Natl. Acad. Sci. U.S.A. 84: 5918-5922; 1987) reported that non-covalently albumin-linked bilirubin is more effective than uric acid in scavenging peroxyl radicals but less efficient in such radical scavenging than Vitamin C.

In Proc. Natl. Acad. Sci., 84: 8130-8134; 1987), Stocker et al. report that ditauro-bilirubin, a di-conjugated form of bilirubin, prevents the peroxyl radical-induced oxidation of phosphatidylcholine in multi-lamellar liposomes or micelles.

Stocker et al. (Biochimica et Biophysica Acta, 1002: 238-244; 1989) describe the synergism between Vitamin E and $B_u$ or biliverdin wherein lipid peroxidation in soybean phosphatidylcholine liposome was prevented.

Robertson et al. (Arch. Biochem Biophys. 213: 353-357; 1982) determined that $B_u$ and biliverdin are directly attacked and oxidized by superoxide.

Substances which have previously been proposed for use as free radical scavengers to reduce ischemia-reperfusion damage include allopurinol, ascorbic acid, dl-tocopherol and vitamin E—see for example U.S. Pat. No. 4,877,810.

It is an object of the present invention to provide a more efficient biomedically acceptable antioxidant for use, inter alia, in reperfusion.

SUMMARY OF THE INVENTION

The present invention is based upon the discovery that protein-bound or peptide-bound bilirubins as exemplified by delta-bilirubin, and delta-bilipeptide as hereinafter defined, are unexpectedly useful and efficient as antioxidant and cytoprotective agents in biomedical applications. Their efficiencies in such applications are much greater than that of any of the other known bilirubins, and greater than that of previously used antioxidants such as trolox and ascorbic acid. They are particularly useful in treating a patient's blood following ischemia, to reduce the damage caused by oxidative free radicals on tissues and organs on re-perfusion thereof with blood after ischemia. Moreover, delta-bilirubin is much more stable in cellular milieu than other forms of bilirubin. Also, it is non-toxic. Further it is persistent, lasting in the bloodstream naturally for several weeks—at least 4-6 weeks.

Whilst it is not intended that this invention should be limited to any particular mode of action or theoretical mechanism, it is believed that the methylene group—$CH_2$—which links the two central pyrrole nuclei in bilirubin is peculiarly stereochemically exposed, due to the peculiar conformation which delta-bilirubin and delta-bilipeptide assume, dictated by the peptide chain attached to the propionic acid side group. In the case of delta-bilirubin, this is natural albumin. In the case of delta-bilipeptide, this is a peptide sequence as found in natural albumin. The methylene group being so stereochemically exposed, is readily oxidizable to a ketone group, rendering it an especially efficient oxygen scavenger or antioxidant.

The present invention in one aspect provides delta-bilirubin and delta-bilipeptides for use as cytoprotective antioxidant agents.

According to another aspect of the invention, there is provided a composition useful as an antioxidant in treating blood in a mammal in vivo to scavenge oxidative free radicals therefrom, said composition comprising effective an amount of delta-bilirubin or bilipeptide in association with a physiologically acceptable adjuvant therefor.

From another aspect, the invention provides a method of decreasing the oxidative free radical concentration in mammalian blood, which comprises treating the mammalian blood in vivo with an effective amount of delta-bilirubin or delta-bilipeptide.

"Delta-bilipeptide" as the term is used herein means a biliprotein having a bilirubin nucleus covalently linked through one of its propionic acid groups via an amide linkage to the epsilon amino group of a lysine unit of a peptide residue as found in natural albumin, said peptide residue having from 12 to about 200 amino acid residues and the lysine units to which the bilirubin nucleus is linked being disposed in a sequence Lys-Gln-Arg, in which Gln represents glutamine and Arg represents arginine.

BRIEF REFERENCE TO THE DRAWINGS

The accompanying figure of drawings FIG. 1A and FIG. 1B are a diagrammatic illustrations of the probable chemical formula and structure of delta-bilirubin.

DESCRIPTION OF THE PREFERRED EMBODIMENTS

Figure 1A:
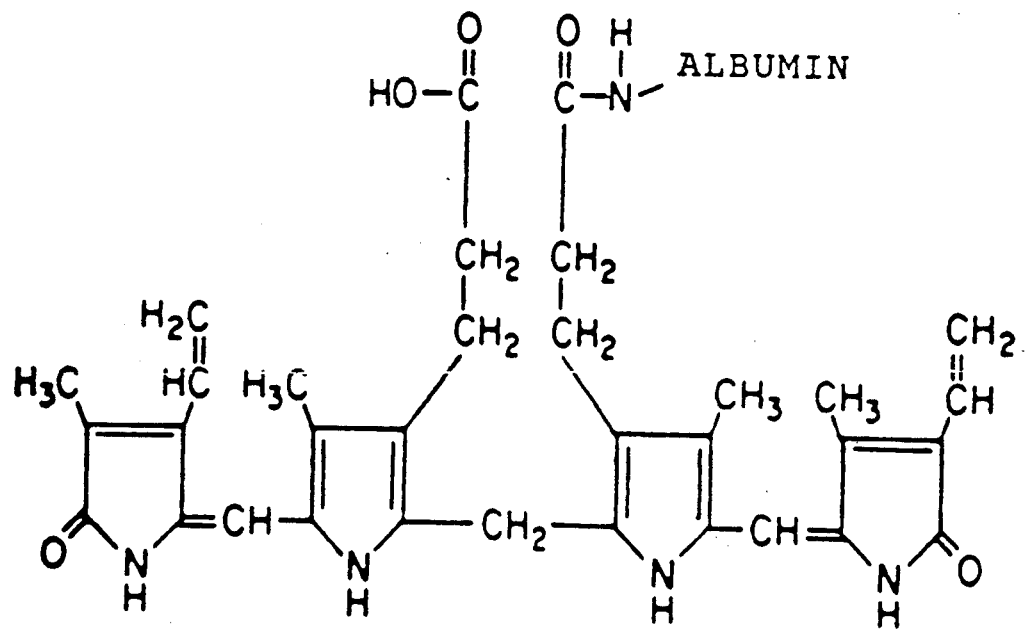
Figure 1B:
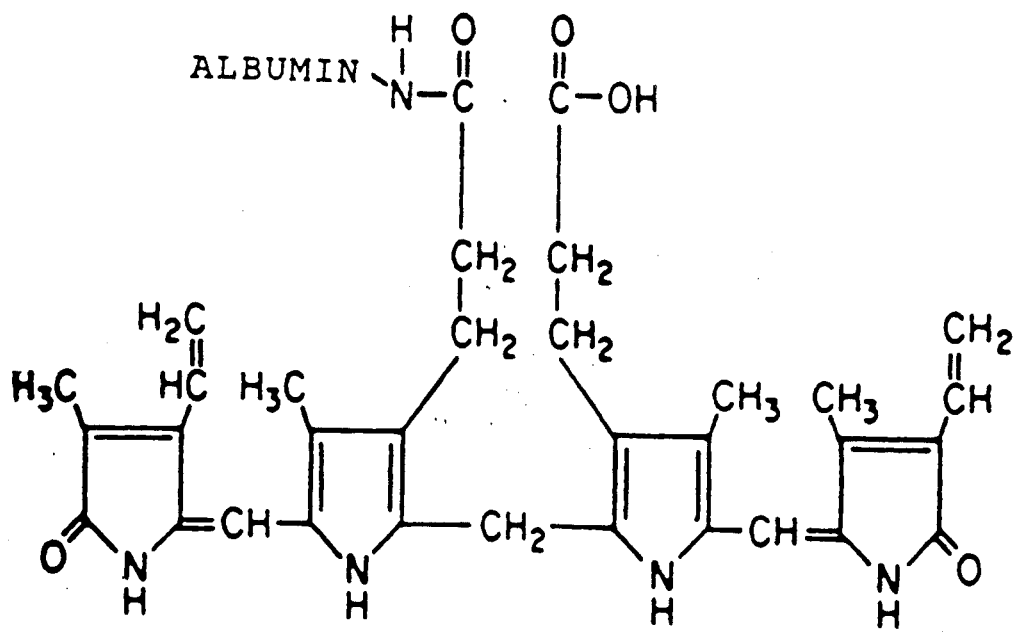

As illustrated in the accompanying Figure, delta-bilirubin consists essentially of a tetrapyrrole nucleus, in which the pyrrole units are linearly arranged and linked by $=CH-$ or $-CH_2-$ bridges. The albumin protein portion is linked through a propionic acid group attached to the pyrrole nucleus, covalently at a specific location along the albumin chain. The albumin protein molecular portion is large (69,000 approximate molecule weight; 585 amino acid residues of known sequence), as compared with the molecular weight of bilirubin of about 585. Delta-bilipeptide may be formed by cleaving off a large portion of the protein chain of albumin from delta-bilirubin, leaving intact the bilirubin-albumin covalent bond and the natural amino acid sequence of albumin adjacent thereto, of from about 12-200 amino acid residues of the attached albumin portion. The sequence Lys-Gln-Arg, in which Lys is the lysine residue to which the bilirubin is attached, must be present.

Delta-bilipeptide can be prepared by site-specific enzymatic cleavage or restriction, or chemical cleavage, of the albumin portion of delta-bilirubin, by methods of site-specific protein cleavage known in the art. Alternatively, a suitable peptide chain can be chemically synthesized by known methods, from individual amino acids, and chemically bonded to the appropriate site on the bilirubin nucleus. In another alternative, albumin isolated from other sources can be subjected to enzymatic or chemical cleavage procedures, to prepare a suitable peptide sequence and then attached covalently by chemical means through the aforementioned lysine group to the bilirubin nucleus. Proteases suitable for selective protein cleavage include papain, pepsin and trypsin. A useful chemical cleavage method utilizes cyanogen bromide CNBr, which specifically cleaves methionine residues.

The preferred process of the present invention is the use of delta-bilirubin or delta-bilipeptide as an antioxidant to reduce organ ischemia-reperfusion injury. For this purpose, an effective amount of the delta-bilirubin or delta-bilipeptide composition, in a suitable physiologically acceptable carrier, in liquid form, is injected into the patient's blood immediately prior to reperfusion of the organ following ischemia, and at a location adjacent to the organ to be reperfused. If such injection takes place adjacent to the organ to be reperfused, lesser amounts of the active ingredient delta-bilirubin or delta-bilipeptide are necessary. Beneficial results can also be obtained by a general injection into the bloodstream of the active ingredients delta-bilirubin and delta-bilipeptide at any convenient location, but this is wasteful, and larger quantities of the active ingredients are then necessary. Sometimes, however, in the case of injured patients, injection at other locations is inevitable. Oral administration with a suitable carrier is also possible.

Suitable physiologically acceptable carriers for the delta-bilirubin and delta-bilipeptide for use in the present invention include water and saline solution, preferably isotonic saline solution, or any commonly used cardioplegic solution, for ready mixing and compatibility with the blood. Most preferred as the carrier for an injectable delta-bilirubin or delta-bilipeptide solution for administration to a patient is a sample of the patient's own blood, or blood of the patient's type. Such is normally available at the site of the ischemia-involving surgery. It provides ideally biocompatible medium for the patient.

The quantities of solid delta-bilirubin or delta-bilipeptide to be administered vary based upon the body weight and blood capacity of the patient. In general, it is preferred to provide a patient with from about 1 mg-50 mg of the material per decilitre of blood circulating in the patient. For a human adult patient of normal body weight and blood capacity, an amount from about 10 mg-200 mg of the delta-bilirubin or delta-bilipeptide is suitable, preferably an amount of from about 50-150 mg. Suitable adjustments can be made to these quantities in proportion to a patient's weight, when administering to children, animals etc.

The concentration of delta-bilirubin or delta-bilipeptide in the solution to be administered is not critical, and can readily be devised by the administrator. Dilute solutions are usually preferred. It is important that the antioxidant solution be administered to the patient slowly, e.g. over a 10-20 minute period, so that a dilute solution is more easily administered under such circumstances. The patient's condition and vital signs should be monitored as the solution is administered, and the rate of administration adjusted if necessary.

Delta-bilirubin, due to the fact that it is naturally found in the body, is therapeutically desirable and acceptable for use as a biomedical antioxidant. Further, its stability and its reactivity with respect to oxidation provide properties highly desirable for its use as such an antioxidant.

Delta-bilipeptide is especially preferred for use in compositions and processes of the present invention. Delta-bilipeptide is a significantly smaller molecule than delta-bilirubin, so that it will more easily and more efficiently penetrate into cells and tissues to effect its function as an antioxidant. At the same time, it retains all of the activity characteristics of delta-bilirubin, enabling it to work as an antioxidant and free radical oxidative scavenger in the present invention.

DETAILED DESCRIPTION OF THE INVENTION

The present invention is described further by means of the following non-limiting examples.

In the following examples BP was isolated and purified from icteric sera as described by Wu in Clin. Chem. (28: 629–637, 1982) and quantitated according to Doumas and Wu (Clin. Chem. 33: 769, 1987).

EXAMPLE 1

Cytoprotective Effect on Rat Hepatocytes

Rat hepatocytes were isolated by the well-known two-step perfusion method of Seglen (Exp. Cell Res. 82: 391–398; 1973) and cultured as per Princen et al. (J. Clin. Invest. 78: 1064–1071; 1986).

The cultured cells were grown to confluency and then pipetted into petri plates such that each plate contained the same number of cells (100,000 cells/plate). The growth media present was removed from each plate and free radical generating media was added to each plate. To the control was added 3 ml phosphate buffered saline (PBS) comprising 2 mM hypoxanthine and $67\mu$/L xanthine oxidase. To the experimental plates was added 3 ml of PBS comprising 8 $\mu$M BP, 2 mM hypoxanthine and $67\mu$/L xanthine oxidase.

The time to necrose 100,000 hepatocytes exposed to free radicals (i.e. the control) was approximately 10 minutes.

The time to necrose hepatocytes in the experimental plates was approximately 44 minutes. The delay in necrosis time of hepatocytes due to the presence of delta-bilirubin was measured in a blind fashion and in triplicate.

EXAMPLE 2

Cytoprotection of Human Myocytes

Myocytes were prepared by incubating 100–400 mg of freshly biopsied human ventricular myocardium with 5–10 mL of a solution containing 0.1% collagenase and 0.2% trypsin in sodium phosphate buffer, free of $Ca^2$. and $Mg^2$. ions and containing 0.9% saline (PBS), pH 7.3, at 37° C. with gentle shaking. After 15–20 minutes, the incubation mixture was decanted into a vial containing an equal volume of Dulbecco's Modified Eagle Medium (DMEM, from Gibco) containing 10% fetal bovine serum and penicillin (100 $\mu$g/ml)-streptomycin (100 $\mu$g/ml). Undigested tissue was treated as above and all incubation mixtures were collected and centrifuged at 5,000 g for 15 minutes. The sedimented cells were suspended in fresh medium and counted in a Neubauer hemocytometer. Then the cells were incubated at 37° C. under 5% $CO_2$ at a concentration of $6 \times 10^5$ M–$8 \times 10^5$ M. Following incubation for 1 hour, the supernatant fluid was transferred to another culture dish. When the cells reached confluence they were separated by trypsin treatment as described above. The cells were ready for experimentation 7–10 days after separation. All other details were as described in Biochem and Cell Biology (1990) Wu et al. (in press).

The myocytes were identified microscopically by their characteristic morphological appearance and by fluorescent staining with monoclonal antibodies specific for actin (Tsukeka, 1987) and human ventricular myosin light chain 1 (Hoffman et al., 1988) respectively. Myocytes of the same generation and age were used to determine the effectiveness of delta-bilirubin as an oxyradical scavenger in preventing cellular necrosis from artificially generated free radicals. Myocyte necrosis was monitored by changes in cell morphology (e.g. sarcolemmal rupture and cytoplasmic shrinkage) and verified by leakage of enzymes, such as lactate dehydrogenase and aspartate amino transferase, into the culture medium.

The cell culture medium was removed from the cells and 3 mL of 0.05M PBS (pH 7.4) containing 300 IU/L xanthine oxidase (XOD) and 1 mM hypoxanthine was added. The cells were incubated at 37° C. Experimental cells were treated with 16 $\mu$M BP. All additions of BP were supplemented to the cells immediately before adding XOD and hypoxanthine.

The basis for determining the effect of delta-bilirubin on the oxyradicals present was the time taken by the XOD-hypoxanthine system to cause necrosis in $10^5$ cells of the same generation within the same culture dish.

The time to necrose 100,000 ventricular myocytes exposed to artificially generated oxyradicals (the control) was approximately 2 minutes. The time to necrose 100,000 myocytes in the presence of 16 $\mu$M BP was greater than 20 minutes.

EXAMPLE 3

In vivo Use of Delta-Bilirubin and Delta-Bilipeptide

A delta-bilipeptide was prepared and used in this study also. A 12-amino acid residue peptide was synthesized which contained the naturally occurring Lys-Gln-Arg sequence of human serum albumin, but not other Lys residues. This was chemically reacted with unconjugated bilirubin Bu, to form a bili-peptide according to this invention, which was isolated and purified by known methods.

Male Sprague-Dawley rats weighting between 0.3–0.4 kg were anesthetized with enflurane (approximately 0.1% in a 1:1 mixture of oxygen: nitrogen, v/v) and were heparinized (100 IU sodium heparin/kg body weight) intravenously. Following a median laparotomy, the hepatic artery and portal vein were clamped for 70 minutes. In exploratory experiments inducing 0–90 minutes of ischemia, a time of 70 minutes was found to give the best compromise between post-surgical survival and extent of liver necrosis. Inducing ischemia for 70 minutes reproducibly resulted in 50% survival of treated animals for at least 48 hours following surgery and 24.5% +/−5.12% hepatic necrosis in the rats. Hepatic necrosis was determined histochemically by staining the tissue with triphenyl tetrazolium chloride after 48 hours of reperfusion. Reperfusion was induced by declamping of the vessels after 70 minutes ischemia, followed by closure of the abdomen and exsanguination of the animals 15 minutes later. The rat livers were then harvested. Twenty-five percent of the damage to the liver was found to be irreversible.

Five minutes prior to inducing reperfusion, the rats were treated with an antioxidant. A comparison between the antioxidants, superoxide dismutase (SOD) and catalase (CAT) in combination, ascorbic acid, delta-bilirubin and the delta-bilipeptide described above was conducted. 15.5-16.0 micromoles of delta-bilirubin in PBS solution was injected into one set of rats. 24,200 IU/L SOD plus 92,000 IU/L of CAT, both in 3 ml of saline was injected into a second set of rats. 2 mM of ascorbic acid in 3 ml of saline was injected into a third set of rats. 10 micromoles of the synthetic delta-bilipeptide was injected into a fourth set of rats, using PBS carrier. Reperfusion was then effected in the rats.

The rat livers were harvested and the extent of hepatic necrosis was determined histochemically as described above. The results of the experiments were as follows:

| Antioxidant | Quantity Injected | Organ Salvage |
| --- | --- | --- |
| SOD + CAT | 24,200 IU/L + 92,000 IU/L | 32% |
| Ascorbic Acid | 2 mmol/L | 10% |
| Delta-Bilirubin | 15.5-16.0 µmol/L | 55% |
| Delta-bilipeptide | 10.0 µmol/L | 63-70% (n = 3) |

I claim:

1. A composition useful as an antioxidant and cytoprotective agent in treating blood in a mammal in vivo to scavenge oxidative free radicals therefrom, said composition comprising an effective amount of a bilirubin attached covalently to a peptide chain of at least 6 amino acid residues and including the sequence Lys-Gln-Arg, in association with a physiologically acceptable adjuvant therefor.

2. Composition according to claim 1 wherein the active ingredient is bilirubin covalently linked to a peptide sequence as found in natural albumin.

3. Composition of claim 1 wherein, in the bilirubin active ingredient, the bilirubin is covalently linked to the peptide chain by an amide linkage formed between the Lys residue of said sequence and a propionic acid group on the tetrapyrrole nucleus of the bilirubin.

4. Composition according to claim 3 wherein the peptide chain of said bilirubin active ingredient has at least 12 amino acid residues.

5. Composition of claim 4 wherein the active ingredient is delta-bilirubin.

6. Composition of claim 4 wherein said peptide chain has from about 12-200 amino acid residues.

7. Composition of claim 6 wherein said peptide chain sequence corresponds to a sequence found in natural albumin.

8. Composition of claim 7 wherein said peptide chain sequence is derived from natural albumin.

9. Composition of claim 6 wherein the active ingredient is a delta-bilipeptide obtained by subjecting delta-bilirubin to site specific enzymatic or chemical cleavage to truncate the albumin portion thereof.

10. Composition of claim 3 wherein the adjuvant is an aqueous fluid.

11. Composition of claim 10 wherein the adjuvant is water, physiological saline or whole blood.

12. A method of decreasing the oxidative free radical concentration in mammalian blood, which comprises treating the mammalian blood in vivo with an effective amount of a composition according to claim 1.

13. The method of decreasing the oxidative free radical concentration in mammalian blood, which comprises treating the mammalian blood in vivo with an effective amount of a composition according to claim 3.

14. The method of decreasing the oxidative free radical concentration in mammalian blood, which comprises treating the mammalian blood in vivo with an effective amount of a composition according to claim 5.

15. The method of decreasing the oxidative free radical concentration in mammalian blood, which comprises treating the mammalian blood in vivo with an effective amount of a composition according to claim 7.

16. A method of decreasing tissue damage in a mammalian organ during reperfusion of said organ with blood following ischemia, which comprises adding to the blood in vivo an effective amount of a composition according to claim 1.

17. A method of decreasing tissue damage in a mammalian organ during reperfusion of said organ with blood following ischemia, which comprises adding to the blood in vivo an effective amount of a composition according to claim 3.

18. A method of decreasing tissue damage in a mammalian organ during reperfusion of said organ with blood following ischemia, which comprises adding to the blood in vivo an effective amount of a composition according to claim 5.

19. A method of decreasing tissue damage in a mammalian organ during reperfusion of said organ with blood following ischemia, which comprises adding to the blood in vivo an effective amount of a composition according to claim 7.

20. A delta-bilipeptide comprising a bilirubin nucleus having covalently linked thereto a peptide chain containing the sequence Lys-Gln-Arg, the covalent linkage being an amide bond between a propionic acid group linked to the tetrapyrrole bilirubin nucleus and the epsilon amino group of the Lys residue of said sequence, said peptide chain having from about 12-200 amino acid residues.

* * * * *